(12) United States Patent
Kozawa (10) Patent No.: US 11,094,399 B2
(45) Date of Patent: Aug. 17, 2021

(54) METHOD, SYSTEM AND PROGRAM FOR ANALYZING MASS SPECTROMETORIC DATA

(75) Inventor: Hiroaki Kozawa, Ohmihachiman (JP)

(73) Assignee: Shimadzu Corporation, Kyoto (JP)

(*) Notice: Subject to any disclaimer, the term of this patent is extended or adjusted under 35 U.S.C. 154(b) by 1091 days.

(21) Appl. No.: 13/979,251

(22) PCT Filed: Jan. 11, 2011

(86) PCT No.: PCT/JP2011/050290
§ 371 (c)(1),
(2), (4) Date: Jul. 11, 2013

(87) PCT Pub. No.: WO2012/095948
PCT Pub. Date: Jul. 19, 2012

(65) Prior Publication Data
US 2013/0282304 A1 Oct. 24, 2013

(51) Int. Cl.
*G16C 20/20* (2019.01)
*H01J 49/00* (2006.01)
(Continued)

(52) U.S. Cl.
CPC .......... *G16C 20/20* (2019.02); *H01J 49/0036* (2013.01); *G01N 27/62* (2013.01);
(Continued)

(58) Field of Classification Search
CPC .... G06F 19/703; G06F 19/16; H01J 49/0036; H01J 49/424; H01J 49/004;
(Continued)

(56) References Cited

U.S. PATENT DOCUMENTS 5,538,897 A * 7/1996 Yates, III ................ C07K 1/00
436/173
6,468,748 B1 * 10/2002 Monforte ............. C12Q 1/6827
210/635
(Continued)

FOREIGN PATENT DOCUMENTS

JP 08124519 5/1996
JP 10142196 5/1998
(Continued)

OTHER PUBLICATIONS

*EPG v. Alstom* (Case Attached).*
(Continued)

*Primary Examiner* — Catherine T. Rastovski
*Assistant Examiner* — Leonard S Liang
(74) *Attorney, Agent, or Firm* — Chris Mizumoto (57) ABSTRACT

Provided is a mass spectrometric data analyzing method for deducing the structure of an unknown substance from data obtained by an MS" analysis, in which a structural candidate having a high degree of freedom for covering a structural change of the known substance can be created. In the mass spectrometric data analyzing method according to the present invention, a candidate of the partial structure of a known substance which is structurally similar to an unknown substance as the target of deduction is created by eliminating a part of the structure of the known substance (Step S1). Previously given candidates of known additional structural parts are individually added to each candidate of the partial structure of the known substance, thus forming various combinations (Step S5). All the structural formulae that can be derived from each combination are created as the structural candidates of the unknown substance (Step S6).

13 Claims, 5 Drawing Sheets

(51) Int. Cl.
  *G01N 27/62* (2021.01)
  *G01N 30/86* (2006.01)
  *G01N 33/68* (2006.01)
(52) U.S. Cl.
  CPC ..... *G01N 30/8675* (2013.01); *G01N 33/6848* (2013.01); *H01J 49/004* (2013.01)
(58) Field of Classification Search
  CPC ............ C07K 2299/00; A61B 5/14532; G01N 27/3271; G01N 30/8624; G01N 30/8631; G01N 27/62; G01N 30/8675; G01N 33/6848
  USPC ................................................ 702/22–23, 27
  See application file for complete search history.

(56) References Cited

U.S. PATENT DOCUMENTS

| | | | | |
|---|---|---|---|---|
| 6,489,121 B1* | 12/2002 | Skilling | G01N 33/6848 | 250/281 |
| 6,599,707 B1* | 7/2003 | Woods, Jr. | G01N 33/53 | 435/7.1 |
| 6,917,037 B2* | 7/2005 | Ootake | H01J 49/0036 | 250/281 |
| 6,934,639 B1* | 8/2005 | Chen | C12Q 1/37 | 702/27 |
| 7,079,956 B2* | 7/2006 | Ramakrishnan | C07K 14/195 | 702/27 |
| 8,884,218 B2* | 11/2014 | Yamaguchi | H01J 49/004 | 250/281 |
| 2001/0007349 A1* | 7/2001 | Nagai | H01J 49/0027 | 250/281 |
| 2002/0125421 A1* | 9/2002 | Yoshinari | H01J 49/063 | 250/281 |
| 2003/0068831 A1* | 4/2003 | Edwards | G01N 33/6878 | 436/518 |
| 2003/0236634 A1* | 12/2003 | Yoshinari | G06F 19/16 | 702/23 |
| 2004/0111228 A1* | 6/2004 | Kobayashi | H01J 49/0036 | 702/81 |
| 2004/0181347 A1* | 9/2004 | Yoshinari | H01J 49/0036 | 702/27 |
| 2005/0063864 A1* | 3/2005 | Sano | G01N 33/6848 | 422/68.1 |
| 2005/0154538 A1* | 7/2005 | Ramakrishnan | G16B 15/00 | 702/20 |
| 2005/0159902 A1* | 7/2005 | Ogata | H01J 49/0036 | 702/30 |
| 2005/0184232 A1* | 8/2005 | Yokosuka | H01J 49/004 | 250/287 |
| 2005/0258355 A1* | 11/2005 | Ogata | G01N 30/8675 | 250/281 |
| 2006/0169889 A1* | 8/2006 | Yokosuka | H01J 49/0031 | 250/288 |
| 2006/0241926 A1* | 10/2006 | Nottebaum | G06F 19/703 | 703/11 |
| 2006/0255263 A1* | 11/2006 | Ishimaru | G01N 30/8675 | 250/288 |
| 2006/0289735 A1* | 12/2006 | Ohtake | H01J 49/02 | 250/282 |
| 2006/0289739 A1* | 12/2006 | Oonishi | H01J 49/40 | 250/287 |
| 2008/0001079 A1* | 1/2008 | Wang | H01J 49/0036 | 250/282 |
| 2008/0067344 A1* | 3/2008 | Yamaguchi | H01J 49/0036 | 250/282 |
| 2008/0073501 A1* | 3/2008 | Yamaguchi | H01J 49/0036 | 250/282 |
| 2008/0128606 A1* | 6/2008 | Grant | G01N 33/78 | 250/282 |
| 2008/0149825 A1* | 6/2008 | Kozlovski | H01J 49/4215 | 250/287 |
| 2009/0105964 A1* | 4/2009 | Yamaguchi | G01N 27/62 | 702/22 |
| 2009/0134325 A1* | 5/2009 | Goldman | G01N 33/6851 | 250/283 |
| 2009/0166522 A1* | 7/2009 | Umemura | H01J 49/0031 | 250/281 |
| 2009/0173876 A1* | 7/2009 | Li | G01N 33/74 | 250/282 |
| 2010/0311176 A1* | 12/2010 | Williamson | G01N 33/6848 | 436/86 |
| 2010/0312489 A1* | 12/2010 | Yamaguchi | H01J 49/0027 | 702/23 |
| 2011/0121172 A1* | 5/2011 | Savitski | H01J 49/0045 | 250/282 |
| 2011/0171619 A1* | 7/2011 | Sweeney | G09B 23/26 | 434/278 |
| 2011/0278449 A1* | 11/2011 | Boecker | G01N 33/6848 | 250/282 |
| 2012/0191685 A1* | 7/2012 | Albar Ramirez | G16B 20/00 | 707/706 |

FOREIGN PATENT DOCUMENTS

| | | |
|---|---|---|
| JP | 2001249114 A | 9/2001 |
| JP | 2006-17570 A | 1/2006 |
| JP | 2007-285719 A | 1/2007 |
| JP | 2007287531 A | 11/2007 |

OTHER PUBLICATIONS

International Search Report dated Mar. 1, 2011 for International Application No. PCT/JP2011/050290 (2 pages).
Examination Report in Japanese Patent Application No. 2012-552551, dated Mar. 18, 2014, 4 pages (2 pages of English Translation and 2 pages of Official copy).
PCT International Application No. PCT/JP2011/050290, International Written Opinion dated Mar. 1, 2011, 9 pages (5 pages of English Translation and 4 pages of Official Copy).
PCT International Application No. PCT/JP2011/050290, International Preliminary Report on Patentability dated Jul. 25, 2013, 12 pages (7 pages of English Translation and 5 pages of Office Action).

* cited by examiner

Fig. 1

Fig. 3A
PARTIAL STRUCTURE OF KNOWN SUBSTANCE

Fig. 3B
ADDITIONAL STRUCTURAL PART

Fig. 3C
STRUCTURAL CANDIDATES OF UNKNOWN SUBSTANCE

METHOD, SYSTEM AND PROGRAM FOR ANALYZING MASS SPECTROMETORIC DATA

TECHNICAL FIELD

The present invention relates to a mass spectrometric data analyzing method for analyzing data obtained by an $MS^n$ analysis in which a precursor ion originating from a sample to be analyzed is dissociated one or a plurality of times and the fragment ions produced by the dissociation are subjected to a mass spectrometry. More specifically, it relates to a method for deducing the structure of an unknown substance similar to a certain substance having a known structure.

BACKGROUND ART

In the field of mass spectrometry using an ion trap mass spectrometer or other apparatuses, a technique called the MS/MS analysis is commonly known. In a typical MS/MS analysis, an ion having a specific mass (or mass-to-charge ratio, to be exact) of interest is selected as a precursor ion (parent ion) from an object to be analyzed. The selected precursor ion is dissociated by collision induced dissociation (CID) to produce fragment ions. The pattern of fragmentation depends on the structure of the original compound. Accordingly, it is possible to obtain information relating to the mass or chemical structure of the ion of interest by performing a mass spectrometry of the fragment ions produced by the dissociation.

In recent years, samples to be analyzed with this type of system have been progressively increasing in molecular weight and becoming more complex in structure (composition). Therefore, depending on the nature of the sample, it is possible that the ion cannot be dissociated into sufficiently small masses by only one stage of a dissociating operation. In such a case, an $MS^n$ analysis may be performed, in which the dissociating operation is repeated a plurality of times (n−1 times), and the eventually obtained fragment ions are subjected to a mass spectrometry (for example, refer to Patent Document 1, 2 or other documents). The aforementioned mass spectrometry of fragment ions by a single dissociating operation is called an $MS^2$ analysis.

One example of the analytical processing for deducing the structure of an unknown substance from data obtained by the previously described $MS^n$ analysis is the so-called pattern matching using a mass spectrum database. A mass spectrum database is a collection of information relating to various kinds of known substances (known compounds), including the data of $MS^n$ spectra obtained by a mass spectrometry using a predetermined ionization method as well as the compound name, molecular weight, composition formula, structural formula and other information of each substance. By the pattern matching of an $MS^n$ spectrum of an unknown substance with those of the known substances under specified search conditions, the structure of the unknown substance can be deduced.

However, even a database having an enormous number of compounds registered therein cannot completely cover all kinds of compounds to be analyzed. This is particularly true of drugs or pesticides as well as their metabolites or the like. These types of compounds have many variations having the same basic skeleton with its components or substituent groups partially replaced by another one (e.g. a methyl group replaced by an ethyl group, or chlorine replaced by boron) and it is impractical to register all variations in a library. Accordingly, it can occur that an unknown substance of interest is not registered in the database. In such a case, it is difficult to deduce the molecular structure of the unknown substance in question.

As already noted, drugs, pesticides and their metabolites or the like have many variations which are similar to each other in overall structure and merely different in a portion of the structure. With respect to this problem, Patent Document 3 discloses a mass spectrometric data analyzing method capable of easily deducing the structure of an unknown substance which is structurally similar to a known substance.

In the method of Patent Document 3, the structure of an unknown substance is deduced by applying a known pattern of structural change of a known substance which is structurally similar to the unknown substance. In this method, initially, the composition formula of an unknown substance is deduced from the mass of the precursor ion, and the structural formula of a known substance similar to the unknown substance is combined with a predetermined pattern of structural change to create a structural candidate from which the same composition formula as the aforementioned composition formula can be derived. For each of the created structural candidates, the data of an $MS^n$ spectrum which will result from that structure is deduced. Based on the deduced data, the structural candidates are ranked in descending order of their probability. Then, $MS^n$ spectrum data of the unknown substance are compared with those of the known substance to search for a fragment ion peak common to both spectra. If a common peak has been found, it is probable that the portion of the structure of the known substance corresponding to that peak is also included in the unknown substance. Accordingly, the structural candidates are narrowed down to those structures which include that partial structure.

BACKGROUND ART DOCUMENT

Patent Document

Patent Document 1: JP-A 10-142196
Patent Document 2: JP-A 2001-249114
Patent Document 3: JP-A 2007-287531

SUMMARY OF THE INVENTION

Problem to be Solved by the Invention

In the method of Patent Document 3, even if the unknown substance to be analyzed is not registered in the database, its structure can be deduced from information relating to a registered substance which is similar to the unknown substance. However, this method has the problem that the structure of an unknown substance which has caused a structural change that is not registered as the structural change pattern cannot be deduced. For example, the structures of drug metabolites are considered to be created by a process in which a structural part of a metabolic precursor is eliminated and a different structural part is subsequently added. In this process, the combination of which structural part will be eliminated and what structural part will be added significantly varies depending on the kind of metabolic precursor, and it is difficult register all the possibilities as the structural change patterns.

The problem to be solved by the present invention is to provide a mass spectrometric data analyzing method for deducing the structure of an unknown substance from the result of an $MS^n$ analysis of the unknown substance and the structural information of a known substance similar to the unknown substance, in which a structural candidate having a high degree of freedom for covering a structural change of the known substance can be created.

Means for Solving the Problems

The present invention aimed at solving the present invention is a mass spectrometric data analyzing method for deducing the structure of an unknown substance from a result of an $MS^n$ analysis of the unknown substance ($n \geq 2$) and structural information of a known substance similar to the unknown substance, including the steps of:

a) creating candidates of a partial structure of the known substance by eliminating a part of a structure of the known substance;

b) creating combinations of the candidates of the partial structure of the known substance and previously given, known candidates of an additional structural part, and selecting, as a candidate of combination, a combination whose total mass matches with the mass of the unknown substance; and c) creating, as a structural candidate of the unknown substance, a structure that can be derived from each of the candidates of combination.

The point of the mass spectrometric data analyzing method according to the present invention is that a structural change of a known substance is understood as the combination of elimination and addition, rather than a predetermined chemical or metabolic reaction, so as to deal with a reaction that causes an unknown structural change.

In the method according to the present invention, candidates of the partial structure of a previously given, known substance are exhaustively created by eliminating each different part of the structure of the known substance, whereas the candidates of the structural part (additional structural part) to be added to the partial structure of the known substance are given beforehand. The reason for this difference in the method of preparing candidates between the elimination and addition is because the types of structural parts that can be eliminated are significantly dependent on the kind of precursor substance for the reaction, while the types of structures that can be added can be limited.

By this method, various combinations of elimination and addition can be created, so that a structural candidate having a higher degree of freedom for the structural change can be created, without being limited to the structural change patterns described in Patent Document 3. Even the structure of a drug metabolite or similar substance having a large number of structural change patterns can be deduced by the present invention.

Step a) may further include the steps of detecting a fragment ion peak and/or a neutral loss common to both an $MS^n$ spectrum of the known substance and an $MS^n$ spectrum of the unknown substance, and narrowing the candidates of the partial structure of the known substance down to a candidate or candidates which include the partial structure of the known substance corresponding to the common fragment ion peak and/or the neutral loss. This operation excludes an unmistakably incorrect candidate and contributes to the reduction of the processing time for the structural deduction.

Step b) may include deriving a composition formula from an $MS^n$ spectrum of the unknown spectrum and selecting, from the combinations of the candidates of the partial structure of the known substance and the candidates of the additional structural parts, a combination, as a candidate of combination, whose composition formula matches with the derived composition formula. (A matching of the composition formulae means a matching of their masses.) Step b) may further include allowing a user skilled in the art to manually select a candidate of the partial structure of the known substance and/or a candidate of the additional structural part to be added to the partial structure.

It is also possible to further provide a step of deducing, for a plurality of structural candidates created in Step c), a fragment ion peak originating from each of the structural candidates and comparing the deduced fragment ion peak to a fragment ion peak of the unknown substance, so as to rank the structural candidates in descending order of their probability of being the structure of the unknown substance. The degree of probability should preferably be numerically evaluated. With these kinds of information, users can easily grasp what types of candidates have been obtained and what degree of reliability each candidate has.

Effect of the Invention

By the mass spectrometric data analyzing method according to the present invention, it is possible to create a structural candidate having a higher degree of freedom for structural change than the structural change patterns described in Patent Document 3. Even the structure of a drug metabolite or similar substance having a large number of structural change patterns can be deduced.

BEST MODE FOR CARRYING OUT THE INVENTION

One embodiment of a mass spectrometric data analyzing system for carrying out the mass spectrometric data analyzing method according to the present invention (which is hereinafter simply called the "data analyzing system") is hereinafter described with reference to the drawings. The following descriptions deal with the case of using a result of an analysis by a liquid chromatograph mass spectrometer. The same discussions also holds true in the case of using a gas chromatograph mass spectrometer or other types of chromatograph mass spectrometers, as well as in the case of using a mass spectrometer into which a sample is directly introduced.

Figure 1:
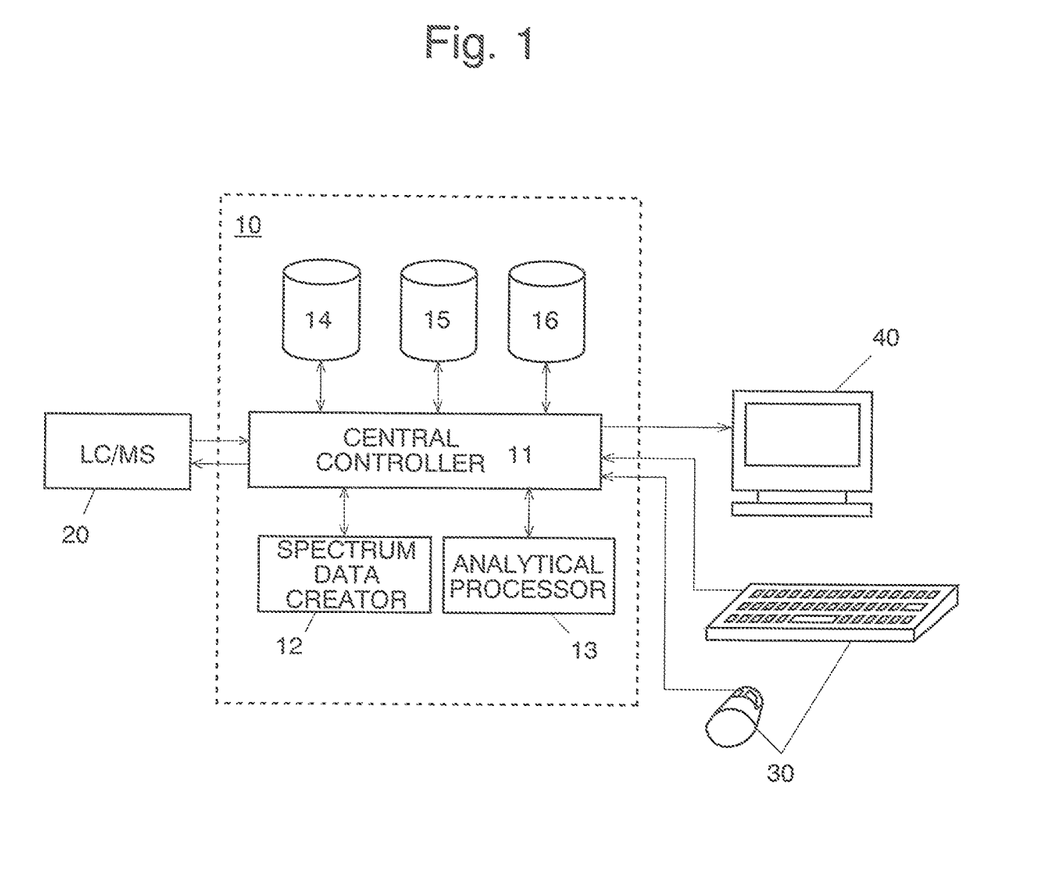
FIG. 1 is schematic configuration diagram showing one example of the system for carrying out the mass spectrometric data analyzing method according to the present invention.

FIG. 1 shows the configuration of the data analyzing system 10 of the present embodiment. The data analyzing system 10, which is used for processing detection data sent from a liquid chromatograph mass spectrometer (LC/MS) 20, includes a central controller 11, a spectrum data creator 12, an analytical processor 13, a measurement data memory 14, a reference data memory 15 and an additional structural part memory 16. The measurement data memory 14, the reference data memory 15 and the additional structural part memory 16 are connected to the central controller 11. An input unit 30 and a display unit 40 are connected to the central controller 11. The central controller 11 also has the function of controlling the operations of each section of the LC/MS 20.

The central controller 11, the spectrum data creator 12 and the analytical processor 13 can be created by a central processing unit (CPU) which operates according to a computer program. For the measurement data memory 14, a readable and writable storage device can be used, such as a hard disk (HD) or magneto-optical disc (MO). The hard disk or similar type of device can also be used for the reference data memory 15 and the additional structural part memory 16, although a read-only device, such as a CD-ROM, may be used as them in a system which requires no recording of data in the reference data memory 15 or the additional structural part memory 16. The reference data memory 15 holds data relating to various kinds of compounds (e.g. the structural formula, composition formula, $MS^n$ spectrum data, and information relating to the partial structure corresponding to each fragment ion peak in the $MS^n$ spectrum data). The additional structural part memory 16 holds information relating to the candidates of the additional structural part to be added to the partial structure of the known substance (e.g. the structural formula, composition formula, mass, and number of charges).

Although the measurement data memory 14, the reference data memory 15 and the additional structural part memory 16 in FIG. 1 are independently provided, these memory units may be created by logically partitioning a single storage device (such as a hard disk). For the input unit 3, a keyboard, mouse and/or other input devices can be used. For the display unit 40, a cathode ray tube (CRT), printer and/or other output devices can be used.

The data analyzing system 10 can be embodied as a controlling and analyzing unit dedicated to an LC/MS system. Alternatively, it may be embodied by installing, in a personal computer or similar multi-purpose computer, a program for performing an analytical method according to the present invention.

The LS/MS 20 is composed of a liquid chromatographic apparatus having a column for temporally separating a mixed sample into components and a mass spectrometer capable of an $MS^n$ analysis (at least an $MS^2$ analysis). Examples of such a mass spectrometer include a triple quadrupole mass spectrometer and an ion trap mass spectrometer. The sample components eluted from the column of the chromatographic apparatus are sequentially ionized and subjected to an $MS^n$ analysis by the mass spectrometer. In this analysis, an ion having an appropriate mass is automatically selected as a precursor ion from the ions originating from the sample components, and the precursor ion is dissociated into fragment ions, which are then made to undergo the mass separation and detection. It is also possible to repeat the selection, dissociation and detection of the ions a plurality of times as needed.

During the measurement of the sample, detection data (digitized detection signals) based on an electric current corresponding to the number of ions detected for each mass are sent from the LC/MS 20 to the data analyzing system 10. The spectrum data creator 12 processes these detection data according to a predetermined algorithm, to compute, at each stage of the $MS^n$ analysis, an $MS^n$ spectrum data consisting of a mass paired with a peak intensity (relative signal intensity) observed at the mass. The obtained data are stored in the measurement data memory 14.

The foregoing descriptions related to the operations of the LC/MS 20 and the data analyzing system 10 during the measurement. The following descriptions, with reference to the flowchart of FIG. 2, explain a procedure of the structural analysis according to the present embodiment using $MS^n$ spectrum data obtained for an unknown substance having a predetermined mass and $MS^n$ spectrum data of a known substance which is structurally similar to the unknown substance, the latter data being stored in the reference data memory 15.

In the present embodiment, the structural analysis is performed on the assumption that a known substance which is structurally similar to the unknown substance is previously known. For example, if the unknown substance to be analyzed is a product of metabolism or chemical change, such as a drug metabolite, and if the precursor used for that reaction is previously known, this precursor can be used as the known substance in the present embodiment. It is also possible to perform a multivariate analysis or similar computation using $MS^n$ spectrum data of the unknown substance and those of the various compounds stored in the reference data memory 15, so as to find a compound considerably similar to the unknown substance in terms of $MS^n$ spectrum data and select that compound as the known substance for the present embodiment.

Figure 2:
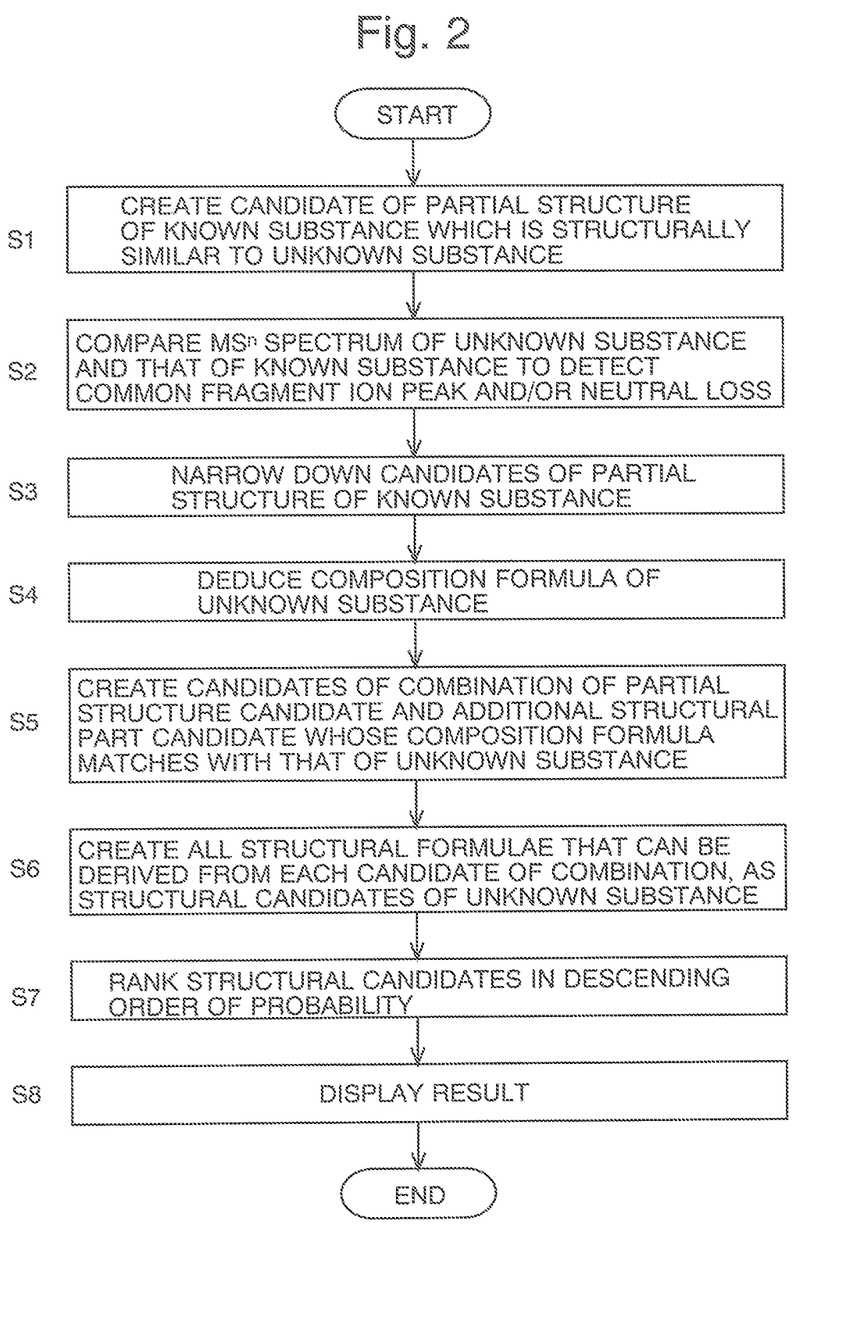
FIG. 2 is a flowchart showing a procedure of the structure analysis of an unknown substance by one embodiment of the mass spectrometric data analyzing method according to the present invention.

For the known substance which is structurally similar to the unknown substance, the analytical processor 13 performs a data processing as follows: Initially, the structural formula of the known substance is retrieved from the reference data memory 15, and candidates of the partial structure are exhaustively created by eliminating each possible part of the structural formula (Step S1). Subsequently, with reference to the $MS^n$ spectrum data of the unknown substance stored in the measurement data memory 14 and those of the known substance stored in the reference data memory 15, a fragment ion peak and/or neutral loss common to the two sets of data is detected (Step S2). Then, the candidates of the partial structure of the known substance created in Step S1 are narrowed down to those which include a partial structure of the known substance corresponding to the fragment ion peak and/or the neutral loss detected in Step S2 (Step S3).

Figure 3A:
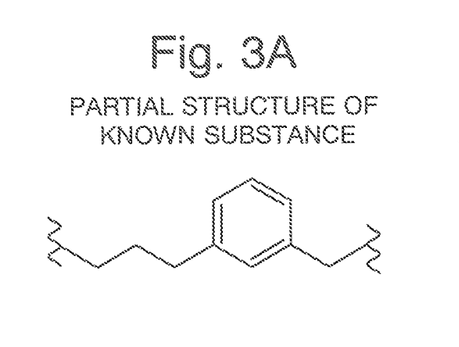
FIGS. 3A-3C are diagrams showing an example of the combination of a candidate of the partial structure of a known substance and a candidate of the additional structural part to be added to it.
Figure 3B:
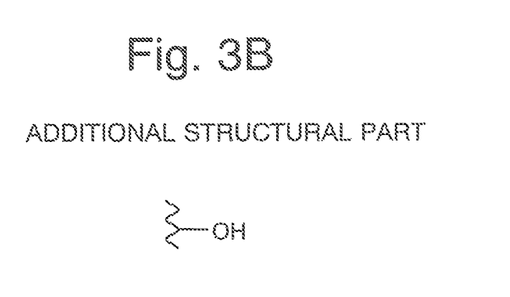
Figure 3C:
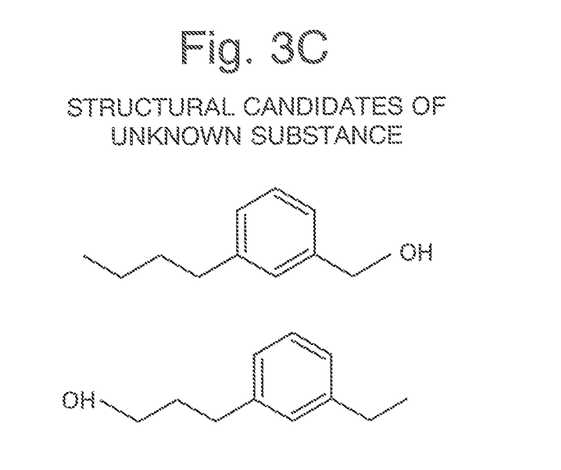

Subsequently, the composition formula of the unknown substance is deduced from its $MS^n$ spectrum data (Step S4). Meanwhile, the candidates of the additional structural part stored in the additional structural part memory 16 are individually added to each candidate of the partial structure of the known substance selected in Step S3, thus forming various combinations, and a combination which matches with the composition formula deduced in Step S4 is created as a candidate of combination (Step S5). Then, all the structural formulae that can be derived from each candidate of combination are created as the structural candidates of the unknown substance (Step S6). FIGS. 3A-3C show one example, in which a hydroxyl group (FIG. 3B) as a candidate of the additional structural part is added to a candidate of the partial structure of a known substance with a single-bond chain at both ends (FIG. 3A). In this example, the bonding of the hydroxyl group can occur at either of the two single-bond chains of the candidate of the partial structure of the known substance (FIG. 3A). Accordingly, two structural formulae can be derived from this candidate of combination. In this manner, there may be a plurality of structural formulae derived from one candidate of combination in Step S6. Conversely, it is possible that no structural formula can be found for some reasons, such as a discrepancy in the number of charges.

Subsequently, for each of the structural candidates of the unknown substance created in Step S6, a fragment ion peak which is expected to be detected in an $MS^n$ analysis is deduced, and the degree of matching of this peak with a fragment ion peak existing in the $MS^n$ spectrum of the unknown substance is numerically expressed as the level of probability. Then, the structural candidates is ranked in descending order of probability (Step S7), and the result is shown on the display unit 40 (Step S8).

Thus far, the mass spectrometric data analyzing method according to the present invention has been described by means of the embodiment. It should be noted that the present invention is not limited to the previous embodiment but can be changed in various ways within the spirit of the present invention.

For example, the mass spectrometric data analyzing method according to the present invention can be performed without the processes of Steps S2, S3 and S7. Furthermore, the process of narrowing down the candidates by the composition formula in Steps S4 and S5 may be achieved by selecting each and every combination whose total mass matches with the mass of the unknown substance.

In the flowchart of FIG. 2, it is assumed that the data analyzing system 10 automatically performs all the steps. However, for example, it is also possible to allow skilled persons to select candidates to be used for the structural deduction from the created candidates of the partial structure of the known substance and the previously given candidates of the additional structural part, based on their own experience. By this method, the processing time for the structural deduction can be reduced if it is to some extent known beforehand which partial structure will remain and which structural part will be added.

FIGS. 4-7 show the result of an experiment of the structural analysis of an unknown substance. In the experiment, an oxygen metabolite of nefazodone was taken as the unknown substance (although its structure was actually known) and nefazodone (the metabolic precursor) as the known substance. The aforementioned selection of candidates by users was performed before the structural analysis was executed.

Figure 4:
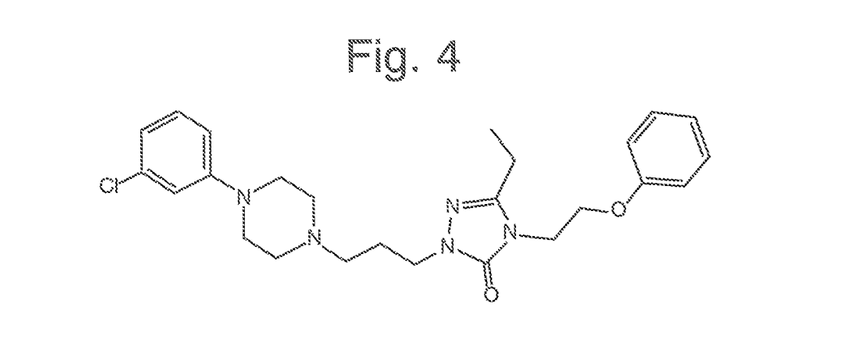
FIG. 4 is a structural formula of nefazodone as the known substance (metabolic precursor).
Figure 5A:
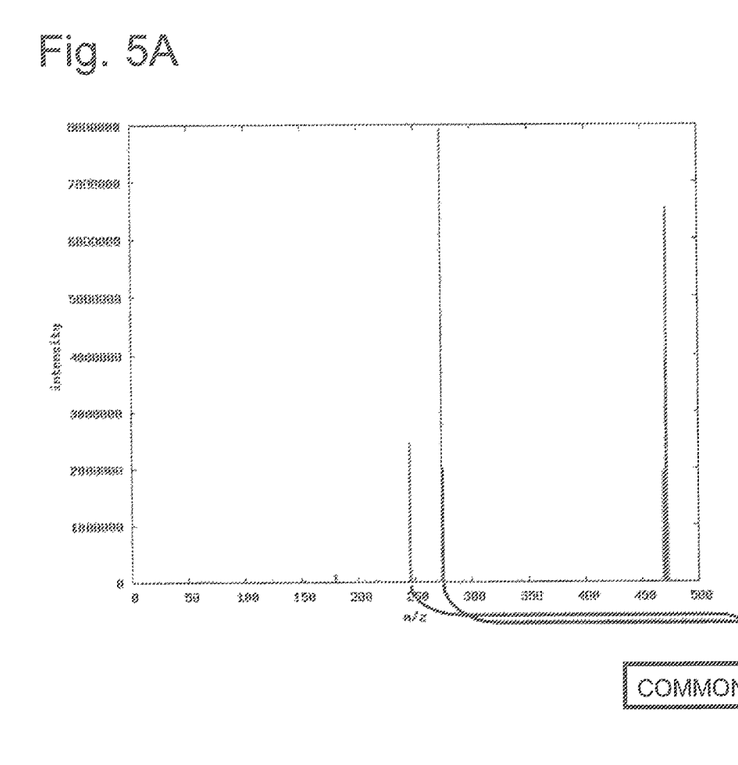
FIG. 5A is an $MS^2$ spectrum of nefazodone as the known substance (metabolic precursor) and FIG. 5B is an $MS^2$ spectrum of an oxygen metabolite of nefazodone as the unknown substance (a product of metabolism).
Figure 5B:
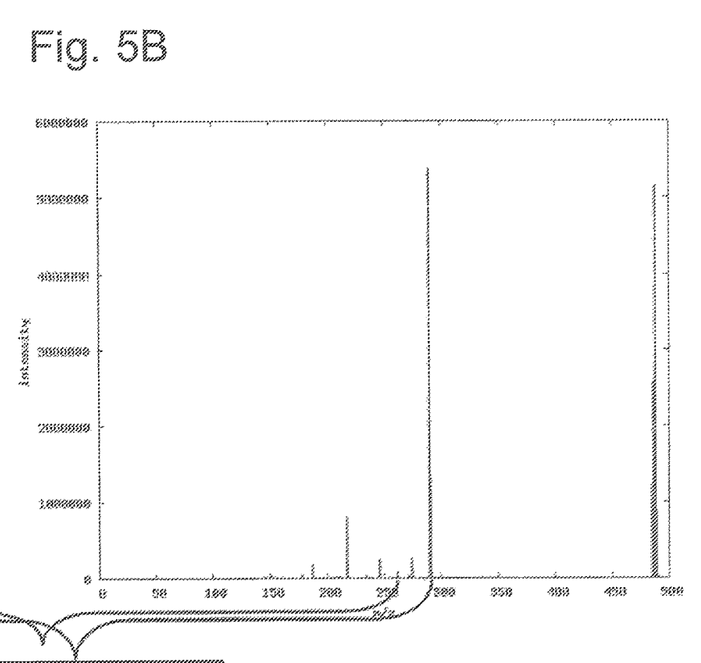
Figure 6A:
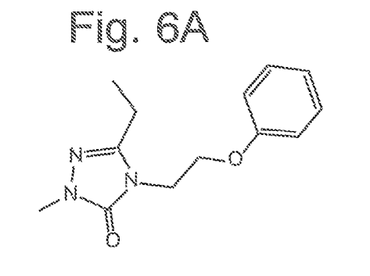
FIGS. 6A-6D are structural formulae of the last candidates of the partial structure of nefazodone.
Figure 6B:
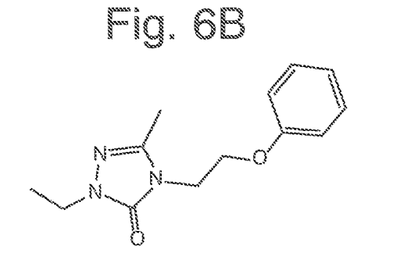
Figure 6C:
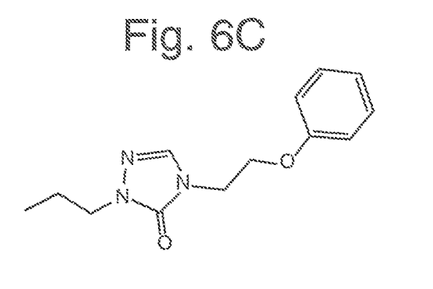
Figure 6D:
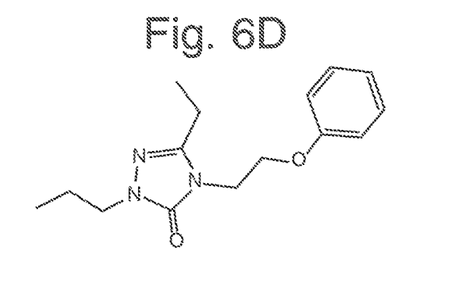
Figure 7:
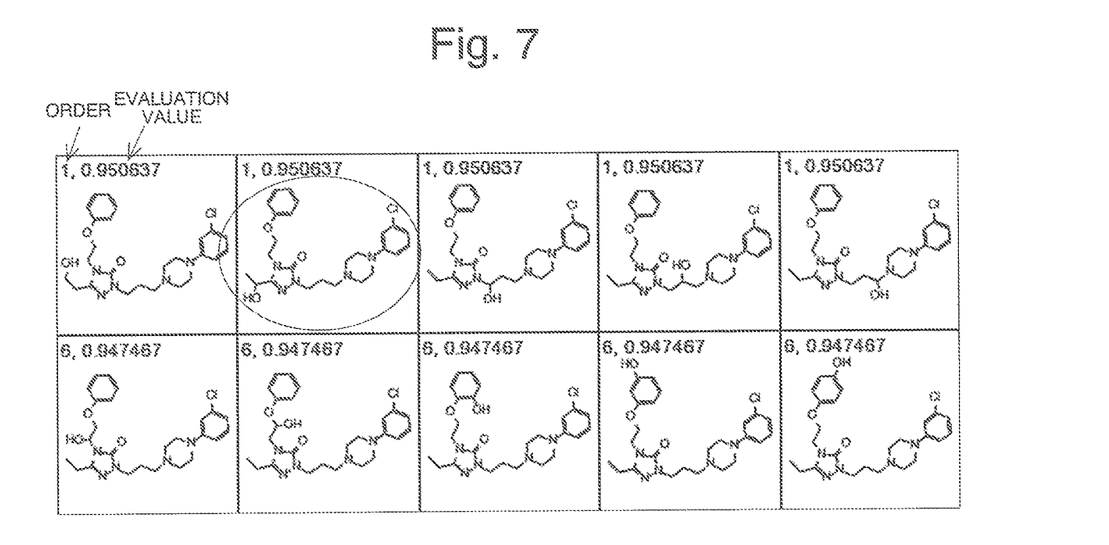
FIG. 7 is a set of structural formulae of the structural candidates of the unknown substance created by the mass spectrometric data analyzing method of the present embodiment.

FIG. 4 is the structural formula of nefazodone as the known substance (metabolic precursor). FIG. 5A is an $MS^2$ spectrum data retrieved from the reference data memory 15. FIG. 5B is an $MS^2$ spectrum data obtained by an $MS^2$ analysis of the oxygen metabolite of nefazodone as the unknown substance (a product of metabolism). FIG. 6A-6D are the structural formulae of the last candidates of the partial structure of nefazodone selected by a user after the candidates of the partial structure created from the structural formula of nefazodone shown in FIG. 4 had been narrowed down by the common neutral losses detected in FIGS. 5A and 5B. FIG. 7 is a set of structural candidates of the unknown substance created by the mass spectrometric data analyzing method of the present embodiment, with the candidates being ranked in order of evaluation value. The evaluation value was obtained by dividing the sum of the intensities of the peaks to which the partial structure was assigned by the sum of the intensities of all the peaks.

As shown in FIG. 7, ten structural candidates of the unknown substance were created in the experiment, and it was confirmed that the structural formula of the oxygen metabolite of nefazodone as the target of deduction was included in them (the second structural formula from the left in the upper row in FIG. 7). The time required for the entire process was 10.7 seconds. Thus, by the mass spectrometric data analyzing method of the present embodiment, the correct structural candidate can be obtained in a practically acceptable processing time even in the structural analysis of a substance having a wide variety of structural change patterns, as in the case of drug metabolites.

EXPLANATION OF NUMERALS

10 . . . Data Analyzing System
11 . . . Central Controller
12 . . . Spectrum Data creator
13 . . . Analytical processor
14 . . . Measurement Data Memory
15 . . . Reference Data Memory
16 . . . Additional Structural Part Memory
20 . . . LC/MS
30 . . . Input Unit
40 . . . Display Unit

The invention claimed is:

1. A mass spectrometric data analyzing method for deducing a structure of an unknown substance from a result of an $MS^n$ analysis of the unknown substance (n≥2) and structural information of a known substance similar to the unknown substance, comprising steps of:
running an $MS^n$ analysis of the unknown substance with a mass spectrometer to generate an $MS^n$ spectrum of the unknown substance;
detecting a fragment ion peak and/or a neutral loss from the $MS^n$ spectrum of the unknown substance, generated by the mass spectrometer;
generating candidates of a partial structure of the known substance by eliminating a part of a structure of the known substance from a structural formula of the known substance, without relying on a predetermined chemical or metabolic reaction of the known substance;
storing known structural parts as candidates of an additional structural part;
creating combinations of the candidates of the partial structure of the known substance and the known candidates of the additional structural part without relying on a predetermined chemical or metabolic reaction of the known substance;
selecting, as a candidate of combination, a combination whose total mass matches with a mass of the unknown substance obtained from the $MS^n$ analysis by running the mass spectrometer; and
creating, as a structural candidate of the unknown substance, a structure that can be derived from each of the candidates of combination.

2. The mass spectrometric data analyzing method according to claim 1, wherein said generating candidates further comprises steps of:
detecting a fragment ion peak and/or a neutral loss common to both an $MS^n$ spectrum of the known substance and an $MS^n$ spectrum of the unknown substance; and narrowing the candidates of the partial structure of the known substance down to a candidate or candidates which include the partial structure of the known substance corresponding to the common fragment ion peak and/or the neutral loss.

3. The mass spectrometric data analyzing method according to claim 1, wherein said creating combinations comprises deriving a composition formula from the MS$^n$ spectrum of the unknown spectrum and selecting, from the combinations of the candidates of the partial structure of the known substance and the candidates of the additional structural parts, a combination, as a candidate of combination, whose composition formula matches with the derived composition formula.

4. The mass spectrometric data analyzing method according to claim 1, further comprising a step of selecting a candidate of the partial structure of the known substance and/or a candidate of the additional structural part to be used in said creating combinations.

5. The mass spectrometric data analyzing method according to claim 1, further comprising steps of:
deducing, for the structural candidates created in said creating a structure, a fragment ion peak originating from each of the structural candidates; and
comparing the deduced fragment ion peak to a fragment ion peak of the unknown substance, so as to rank the structural candidates in descending order of their probability of being the structure of the unknown substance.

6. The mass spectrometric data analyzing method, according to claim 1, wherein the step of generating candidates of a partial structure of the known substance by eliminating a part of a structure of the known substance from a structural formula of the known substance, does not rely on a predetermined chemical or metabolic reaction of the known substance so as to deal with a reaction that causes an unknown structural change of the unknown substance.

7. A mass spectrometric data analyzing system for deducing a structure of an unknown substance from a result of an MS$^n$ analysis of the unknown substance (n≥2) and structural information of a known substance similar to the unknown substance, comprising:
a known substance memory in which a data of a structural formula of the known substance is stored;
an additional structural part memory in which a data of a structural formula of a candidate of an additional structural part is stored;
a partial structure candidate generator for generating a candidate of a partial structure of the known substance, using the structural formula of the known substance retrieved from the known substance memory, without relying on a predetermined chemical or metabolic reaction of the known substance;
a combination candidate creator for creating combinations of the candidates of the partial structure of the known substance and the candidates of an additional structural part, without relying on a predetermined chemical or metabolic reaction of the known substance, and for selecting, as a candidate of combination, a combination whose total mass matches with a mass of the unknown substance; and
a structural candidate creator for creating, as a structural candidate of the unknown substance, a structure that can be derived from each of the candidates of combination.

8. The mass spectrometric data analyzing system according to claim 7, wherein:
the known substance memory further holds a data of an MS$^n$ spectrum of the known substance and a data of the partial structure of the known substance corresponding to a fragment ion peak and/or a neutral loss on the MS$^n$ spectrum; and
the partial structure candidate creator further comprises:
a detector for detecting a fragment ion peak and/or a neutral loss common to both an MS$^n$ spectrum of the known substance and an MS$^n$ spectrum of the unknown substance; and
a structural candidate narrowing section for narrowing the candidates of the partial structure of the known substance down to a candidate or candidates which include the partial structure of the known substance corresponding to the common fragment ion peak and/or the neutral loss.

9. The mass spectrometric data analyzing system according to claim 7, wherein the combination candidate creator derives a composition formula from an MS$^n$ spectrum of the unknown spectrum, and selects, from the combinations of the candidates of the partial structure of the known substance and the candidates of the additional structural parts, a combination, as a candidate of combination, whose composition formula matches with the derived composition formula.

10. The mass spectrometric data analyzing system according to claim 7, wherein the combination candidate creator further comprises a candidate selector for allowing a user to select a candidate of the partial structure of the known substance and/or a candidate of the additional structural part to be used in the combination candidate creator.

11. The mass spectrometric data analyzing system according to claim 7, further comprising a rank determiner for deducing, for a plurality of structural candidates created by the structural candidate creator, a fragment ion peak originating from each of the structural candidates, and for comparing the deduced fragment ion peak to a fragment ion peak of the unknown substance, so as to rank the structural candidates in descending order of their probability.

12. A mass spectrometric data analyzing program for making a computer function as the mass spectrometric data analyzing system according to claim 7.

13. The mass spectrometric data analyzing system, according to claim 7, wherein the partial structure candidate generator for generating a candidate of a partial structure of the known substance, using the structural formula of the known substance retrieved from the known substance memory, does not rely on a predetermined chemical or metabolic reaction of the known substance so as to deal with a reaction that causes an unknown structural change of the unknown substance.

* * * * *